United States Patent [19]
Buck et al.

[11] Patent Number: 5,830,863
[45] Date of Patent: Nov. 3, 1998

[54] NEUROKININ A ANTAGONISTS

[75] Inventors: Stephen H. Buck; Scott L. Harbeson, both of Cincinnati, Ohio; John L. Krstenansky, Palo Alto, Calif.; Chester F. Hassman, III, Durham, N.C.; James R. McCarthy, West Chester, Ohio

[73] Assignee: Merrell Pharmaceuticals Inc., Cincinnati, Ohio

[21] Appl. No.: 764,157

[22] Filed: Dec. 13, 1996

Related U.S. Application Data

[63] Continuation of Ser. No. 637,013, Apr. 24, 1996, abandoned, which is a continuation of Ser. No. 282,340, Jul. 29, 1994, abandoned, which is a continuation of Ser. No. 6,200, Jan. 19, 1993, abandoned, which is a continuation of Ser. No. 686,593, Apr. 17, 1991, abandoned, which is a continuation-in-part of Ser. No. 356,031, May 23, 1989, abandoned, which is a continuation-in-part of Ser. No. 315,202, Feb. 24, 1989, abandoned, which is a continuation of Ser. No. 208,926, Jun. 20, 1988, abandoned.

[51] Int. Cl.$^6$ ..................................................... A61K 38/00
[52] U.S. Cl. .............................. 514/16; 514/15; 514/21; 514/826; 530/328; 530/329; 530/332
[58] Field of Search ............................... 514/15, 16, 21, 514/826; 530/328, 329, 332

[56] References Cited

U.S. PATENT DOCUMENTS

| | | | |
|---|---|---|---|
| 4,242,256 | 5/1988 | Sharpe et al. | 260/112.5 R |
| 4,439,360 | 3/1984 | Verdini | 530/331 |
| 4,609,643 | 9/1986 | Szelke et al. | 514/16 |
| 4,638,047 | 1/1987 | Szelke et al. | 530/332 |
| 4,665,157 | 5/1987 | Wright et al. | 530/328 |
| 4,680,283 | 7/1987 | Veber et al. | 514/17 |
| 4,742,156 | 5/1988 | Wright et al. | 530/328 |
| 5,084,555 | 1/1992 | Coy et al. | 530/328 |
| 5,236,921 | 8/1993 | Emonds-Alt | 514/252 |
| 5,317,020 | 5/1994 | Emonds-Alt | 514/255 |
| 5,521,156 | 5/1996 | Owen et al. | 514/11 |

FOREIGN PATENT DOCUMENTS

| | | |
|---|---|---|
| 0109142 | 5/1984 | European Pat. Off. . |
| 0176436 | 4/1986 | European Pat. Off. . |
| 0219258 | 4/1987 | European Pat. Off. . |
| 0401177 | 5/1990 | European Pat. Off. . |
| 0393989 | 10/1990 | European Pat. Off. . |
| 0394989 | 10/1990 | European Pat. Off. . |
| 0401507 | 12/1990 | European Pat. Off. . |
| 0428434 | 5/1991 | European Pat. Off. . |
| 2010246 | 6/1983 | Germany . |
| 9003980 | 4/1990 | WIPO . |
| 9109844 | 7/1991 | WIPO . |

OTHER PUBLICATIONS

Sandberg, et al., Proc. Eur. Pept. Symp., 18th 369–372 (1984).
Mazrahi, et al., Eur. J. Pharmacol. 118:1–2, 25–36 (1985).
Reifenrath, et al., J. Med. Chem. 23:985–90 (1980).
Gao, et al., J. Med. Chem. 33:39–44 (1990).
Steinman, J. Med. Chem. 16(12):1354–60 (1973).
Barnes, Lancet 242–244 (Feb. 1, 1986).
Payan, et al., Am. Rev. Respir. Dis 136:539–34 (1987).
Devillier, et al., Inflammatory Diseases, vol. 314(20):1323.
The Merck Manual of Diagnosis and Therapy, 11th edition, 1076–1078 (1966).
Rosell, Subs. P. Metab. Biol. Actions (Proc Symp) Mtg in 1984, 95–97 (1985).
Abu Shanab, et al., Biochem Soc. Trans. 17(4), 731–2 (1989).
Harbeson, et al., J. of Cellular Biochemistry Supplement 14C, p. 242, (CK305) 1990.
Snider, et al., Chemistry & Industry, Nov. 4, 1991.
Logan, et al., Annual Reports in Medicinal Chemistry 26, Chapter 5, p. 43.
Dion, et al., Life Sciences 41, 2269–2278 (1987).
McLean, et al., Biochemica Et Biophysica Acta, vol. 1024, 1–4 (1990).
Dutta, A.S., Drugs of the Future, vol. 12(8), 781–792 (1987).
Coy, D.H., et al., The J. of Biol. Chem., vol. 263(11), 5056–5060 (1988).
Cowan, A., et al., Peptides in Health and Disease, Italy, 13–16 Oct. 1987. Trends in Pharm. Sci. 9(1):1–3, (Jan. 1988).
Regoli, Chem Abst 107:109366C (1987), Int.Congr.Ser.–Excerpta Med. 731, 85–95 (1987).
Regoli, et al., Chem Abst 107:1525q, (1987) (5th Annu. Wash.Spring Symp.Health Sci.J.), 501–11(1986).
Hashimoto, Chem Abst 107:211967m, (1987), Chem. Pharm.Bull. 35(8), 3442–6(1987).
Hashimoto, et al., Chem Abst 108:32646e, Jpn. J. Pharmacology, 45(4), 570–3 (1987).
Ewenson, et al., Chem Abst 106 102664u (1985),, Proc. 9th Am. Pept. Symp.,639–42 (1987).
Cox, et al., Chem Abst 94:31068y (1981), J.Chem.Soc., Chem. Commun. 17, 800–2 (1980).
Buck, et al., Neuroscience Abst. 14:144 (1988), 18th Ann.Meeting for the Soc.for Neuroscience, Nov. 12–18 (1988).
Buck, et al., Chem Abst 109(11):86429a (1988), Life Sci., 42(26), 2701–8 (1988).
Rovero, et al., Chem Abst 111(13):109167w, Peptides 10(3), 593–5 (1989).
Rovero, et al., Chem Abstr 111(9):71117q (1989), Neuropeptides 13(4), 263–70 (1989).
Hashimoto, et al., Chem.Abst 107:21 (1987) 237277n.
Drapeau, et al., Chem Abst 107(19) 168939q (1987), Neuropeptides 10(1), 43–54 (1987).

(List continued on next page.)

Primary Examiner—Cecilia J. Tsang
Assistant Examiner—C. Delacroix-Muirheid
Attorney, Agent, or Firm—T. Helen Payne

[57] ABSTRACT

Antagonists of neurokinin A which are derivatives of naturally occurring neurokinin A in which the amide bond connecting the two amino acids on the carboxy terminal end is modified are described. The antagonism is confirmed using conventional competitive binding and biochemical assays as well as conventional physiological tests and the use of these derivatives in a variety of conditions in which neurokinin A is implicated is also described.

17 Claims, 5 Drawing Sheets

OTHER PUBLICATIONS

Osakada, et al, Chem Abst 104(17): 142380p, Eur.J.Phrmacol. 120(2), 201–8 (1986).
Drapeau, et al., Chem. Abst 111:9 (1988) 71105j.
Bristow, et al., Br. J. Pharmac 90:211–217 (1987).
Holladay et al., Tetrahedron Letters 24:41, 4401–04 (1983).
Sasaki et al., Peptides 8, 119–121 (1987).
TenBrink, et al., J. Org. Chem. 52, 418–422 (1987).
Buck et al., Science 226, 987–989 (1984).
Spatola et al., Tetrahedron 44(3):821–33 (1988).
Chorev, et al., Int. J. Peptide Protein Res. 21:258–68 (1983).
Gisin, Helvetica Chimica Acta 56(5): 1476–82 (1973).
Kaiser, et al., Short Communications 595–598 (1969).
Sandberg, et al., Proc. Eur. Pept. Symp., 18th 369–372 (1984).
Mazrahi, et al., Eur. J. Pharmacol. 118:1–2, 25–36 (1985).
Harbeson et al., Peptides: Chemistry, Structures & Biology, Proceedings of the 11th American Peptides Symposium, Jul. 9–14, 1989.
Reifenrath, et al., J. Med. Chem. 23:985–90 (1980).
Gao, et al., J. Med. Chem. 33:39–44 (1990).
Steinman, J. Med. Chem. 16(12): 1354–60 (1973).
Barnes, Lancet 242–244 (Feb. 1, 1986).
Payan, et al., Am. Rev. Respir. Dis 136:539–34 (1987).
Devillier, et al., Inflammatory Diseases, vol. 314(20): 1323.
Dubreuil, et al., Drug Design and Delivery 2, 49–54 (1987).
Aumelas, et al., Int. J. Peptide Protein Res. 30:596–604 (1987).
Rovero, et al., Peptides 11:619–20 (1990).
Martinez, et al., J. Med. Chem. 28:1874–79 (1985).
Sasaki, et al., J. Med. Chem. 30:1162–66 (1987).
Morensen and Boyd, Organic Chemistry, 3rd edition, Chapter 3, pp. 79–82 (1974).
The Merck Manual of Diagnosis and Therapy, 11th edition, 1076–1078 (1966).
Abu Shanab, et al., Biochem Soc. Trans. 17(4), 731–2 (1989).
Snider, et al., Chemistry & Industry, Nov. 4, 1991.
Logan, et al., Annual Reports in Medicinal Chemistry 26, Chapter 5, p. 43.
Dion, et al., Life Sciences 41, 2269–2278 (1987).
McLean, et al., Biochimica Et Biophysica Acta, vol. 1024, 1–4 (1990).
Swistok, et al., Tetrahedron Letters, vol. 30(8):5045–5048 (1989).

NEUROKININ A ANTAGONISTS

CROSS-REFERENCE TO RELATED APPLICATION

This is a continuation of application Ser. No. 08/637,013, filed Apr. 24, 1996; now abandoned, which is a continuation of application Ser. No. 08/282,340, filed Jul. 29, 1994, now abandoned; which is a continuation of application Ser. No. 08/006,200 filed Jan. 19, 1993, now abandoned; which is a continuation of application Ser. No. 07/686,593 filed Apr. 17, 1991, now abandoned; which is a Continuation-In-Part of application Ser. No. 07/356,031 filed May 23, 1989, now abandoned; which is a Continuation-In-Part of application Ser. No. 07/315,202 filed Feb. 24, 1989, now abandoned; which is a continuation of application Ser. No. 07/208,926, filed Jun. 20, 1988, now abandoned; which is herein incorporated by reference.

FIELD OF THE INVENTION

This invention relates to novel peptide derivatives which are antagonists of neurokinin A (NKA).

BACKGROUND OF THE INVENTION

Substance P and related tachykinins, neurokinin A and neurokinin B, are a group of naturally occurring peptides shown to have wide distribution within body tissue and a wide variety of biological effects. While agonists and antagonists of substance P and neurokinin B are known and while agonists of neurokinin A are known as well, antagonists of neurokinin A have not yet been reported. Applicants have now discovered a class of neurokinin A antagonists. Such compounds are not only interesting from a biochemical viewpoint, but such compounds also have valuable pharmacological and medical utilities.

SUMMARY OF THE INVENTION

Peptide derivatives of the following structure 1 are antagonists of neurokinin A:

$$X-A_1-A_2-A_3-A_4-A_5-A_6-Y \qquad 1$$

wherein X is hydrogen, an alkyl group of from 1 to 6 carbon atoms, or an acyl group of from 2 to 10 carbon atoms;

$A_1$ is a bond or is a group consisting of from 1 to 4 amino acids;

$A_2$ is a bond or is Asp or Glu;

$A_3$ is any amino acid;

$A_4$ is Phe or N-Me-Phe;

$A_5$ is Ile, Val, Leu, Phe, Ala, Tyr, Nle, Met, or N-Me-Val;

$A_6$ is Gly, B-Ala or Sar; and

Y is a group of the formula $$-NH-\underset{H}{\overset{R_1}{|}}B-\underset{H}{\overset{R_2}{|}}CONH_2$$

wherein B is a group of one of the formulae $-CH_2-N-$, $-CH_2-S-$, $-CH_2-O-$,
  $\underset{R}{|}$ -continued
$-CH=CH-$, $-\overset{O}{\overset{\|}{C}}-CH_2-$, $-CH(OH)CH_2-$, and $-NH-\overset{O}{\overset{\|}{C}}-$, $-CH_2-\overset{O}{\overset{\|}{S}}-$, and wherein R is a hydrogen atom or an alkyl group of from 1–5 carbon atoms or is a phenylalkylidene group wherein the alkylidene moiety is straight or branched and has from 1 to 6 carbon atoms and wherein the phenyl moiety is unsubstituted or is mono substituted with a $C_{1-4}$ alkyl, $C_{1-4}$ alkoxy, hydroxy, or halogen group;

$R_1$ and $R_2$ are each independently selected from isopropyl, isobutyl, sec-butyl, n-butyl, benzyl, and 2-(methylthio)ethyl groups or a pharmaceutically acceptable salt thereof. These novel peptide derivatives are antagonists of neurokinin A and are thus useful antiasthma, antiinflammatory, and antiarthritic agents.

—●—NKA
—●—NKA(3–10)
—▲—NKA(4–10)
—▲—H-Asp-Ser-Phe-Val-Gly-LeuΨ($CH_2NH$)Leu-$NH_2$ (ID#2)
—□—H-Asp-Ser-Phe-Val-Gly-LeuΨ($CH_2NCH_3$)Leu-$NH_2$ (ID#3)

Agonists tested were NKA and fragments of NKA consisting of the third to tenth (NKA(3–10)) amino acids and the fourth to tenth (NKA(4–10)) amino acids. Values are MEAN±S.E.M. of 6–12 experiments. $IC_{50}$ values estimated graphically from 50% inhibition point.

Figure 1:
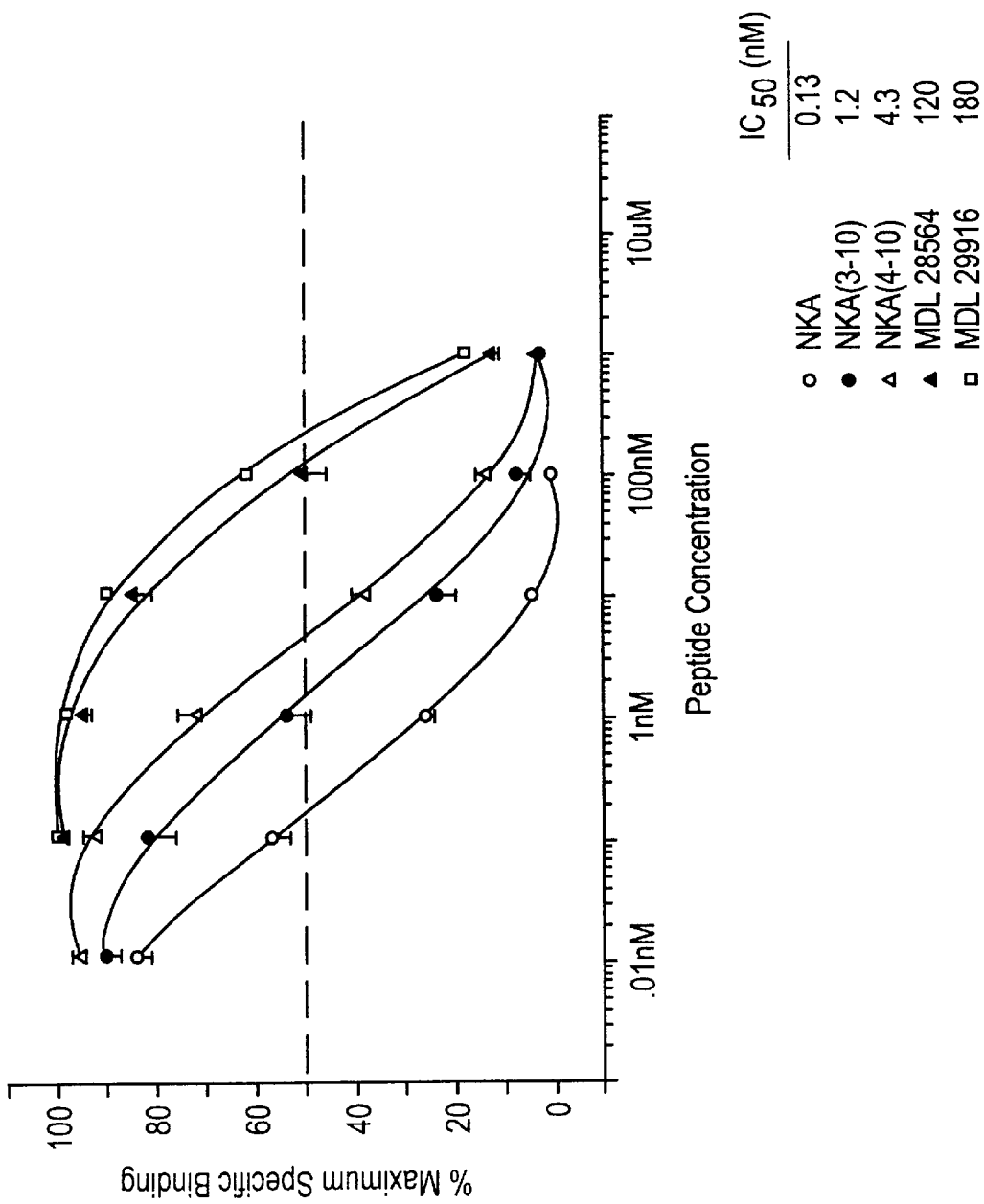
FIG. 1 illustrates the ability of H-Asp-Ser-Phe-Val-Gly-LeuΨ($CH_2NH$)Leu-$NH_2$(ID#2) and H-Asp-Ser-Phe-Val-Gly-LeuΨ($CH_2NCH_3$)Leu-$NH_2$(ID#3) to antagonize binding at the NKA receptor as demonstrated by the ability of test compound to displace $I_{125}$ labeled NKA from hamster urinary bladder (Example 1). The abscissa (x-axis) logarithmically indicates the concentration in nanomoles of agonist of antagonist of the neurokinin A (NKA) receptor. The ordinate (Y-axis) indicates the observed specific binding for each tested agonist or antagonist measured as a percentage of maximum specific binding.
Figure 2:
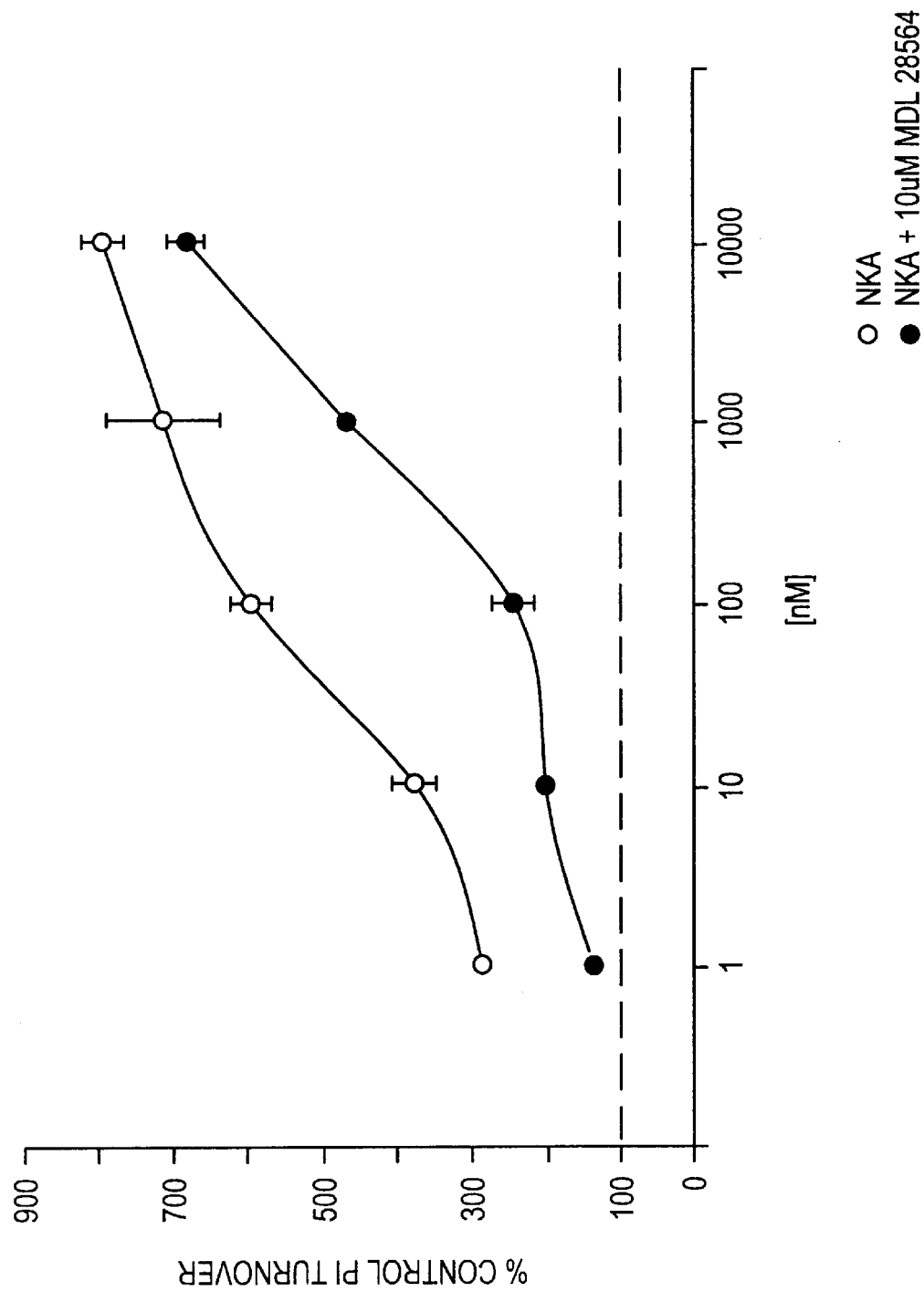

FIG. 2 illustrates the ability of H-Asp-Ser-Phe-Val-Gly-LeuΨ($CH_2NH$)Leu-$NH_2$(ID#2) to antagonize NKA receptor binding as demonstrated by the effect on phosphatidylinositol (PI) turnover in hamster urinary bladder (Example 2). The abscissa (x-axis) logarithmically indicates the concentration in nanomolar (nM) of agonist or antagonist of the NKA receptor. The ordinate (y-axis) indicates the observed PI turnover as a percentage of control.

—●—NKA
—●—NKA+10 μM H-Asp-Ser-Phe-Val-Gly-LeuΨ($CH_2NH$)-Leu-$NH_2$(ID#2)
10 μM H-Asp-Ser-Phe-Val-Gly-LeuΨ($CH_2NH$)Leu-$NH_2$ (ID#2) produced a significant rightward shift of NKA dose-response curve in competitive manner. Values are MEAN±S.E.M. from one experiment in triplicate.

Figure 3:
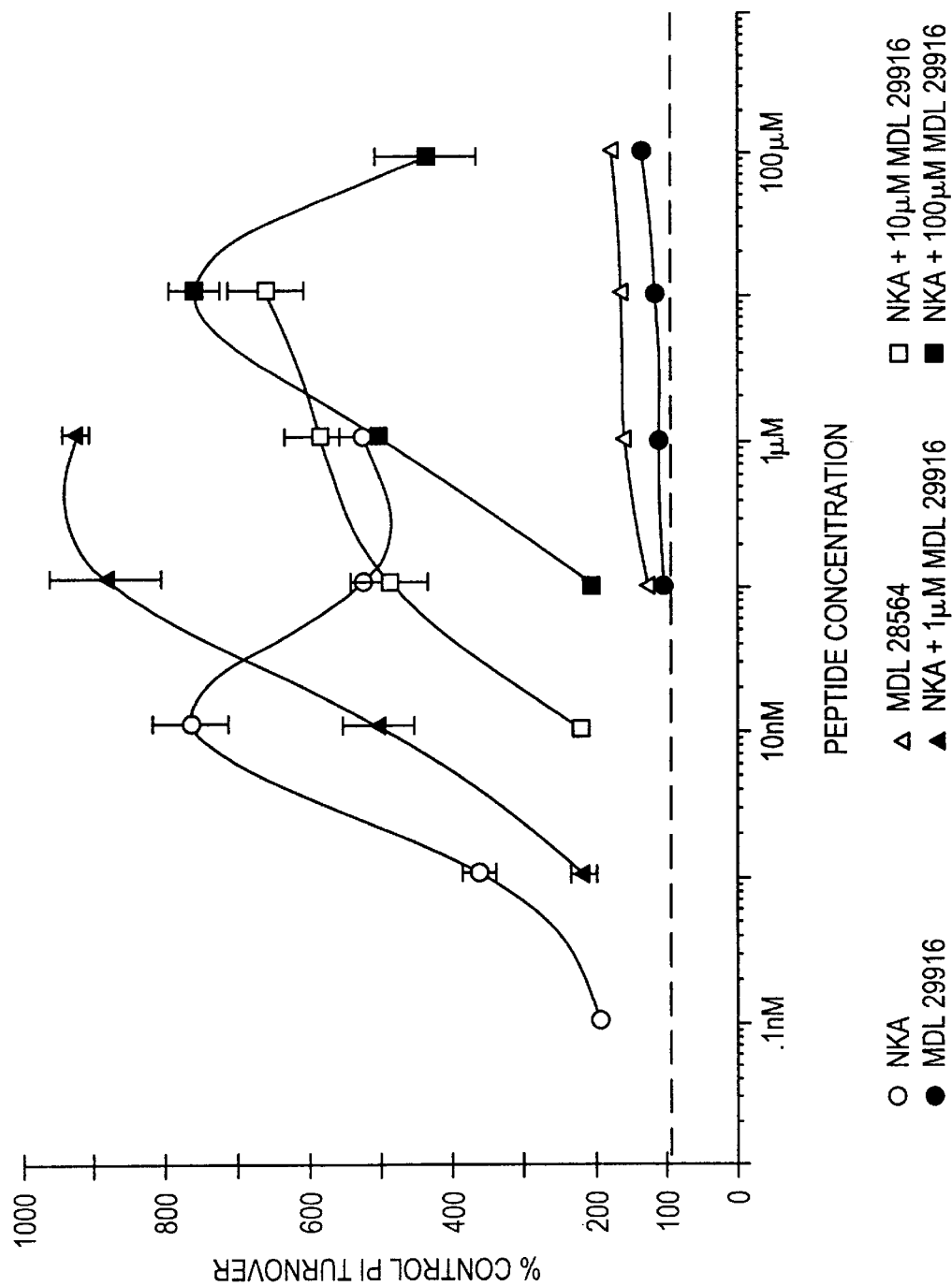

FIG. 3 illustrates the ability of H-Asp-Ser-Phe-Val-Gly-LeuΨ($CH_2NCH_3$)Leu-$NH_2$(ID#3) (MDL 29,916) to antagonize NKA receptor binding as demonstrated by the effect on phosphatidylinositol (PI) turnover in hamster urinary indicates the concentration in nanomolar (nM) of agonist or antagonist of the NKA receptor. The ordinate (y-axis) indicates the observed PI turnover as a percentage of control.

—○—NKA
—●—H-Asp-Ser-Phe-Val-Gly-LeuΨ(CH₂NCH₃)Leu-NH₂ (ID#3)
—▲—H-Asp-Ser-Phe-Val-Gly-LeuΨ(CH₂NH)Leu-NH₂ (ID#2)
—▲—NKA+1 μM H-Asp-Ser-Phe-Val-Gly-LeuΨ(CH₂NCH₃)Leu-NH₂(ID#3)
—☐—NKA+10 μM H-Asp-Ser-Phe-Val-Gly-LeuΨ(CH₂NCH₃)Leu-NH₂(ID#3)
—■—NKA+100 μM H-Asp-Ser-Phe-Val-Gly-LeuΨ(CH₂NCH₃)Leu-NH₂(ID#3)

1, 10 and 100 μM H-Asp-Ser-Phe-Val-Gly-LeuΨ(CH₂NCH₃)Leu-NH₂(ID#3) produced a significant rightward shift of NKA dose-response curve in competitive manner. The Schild plot of these data had slope of −0.99 indicating competitive antagonism and pA2 of 7.66. H-Asp-Ser-Phe-Val-Gly-LeuΨ(CH₂NCH₃)Leu-NH₂(ID#3) up to 100 μM had only 5% partial agonist activity, and H-Asp-Ser-Phe-Val-Gly-LeuΨ(CH₂NH)Leu-NH₂(ID#2) had only 12% partial agonist activity. Values are MEAN±S.E.M. from one experiment in triplicate.

Figure 4:
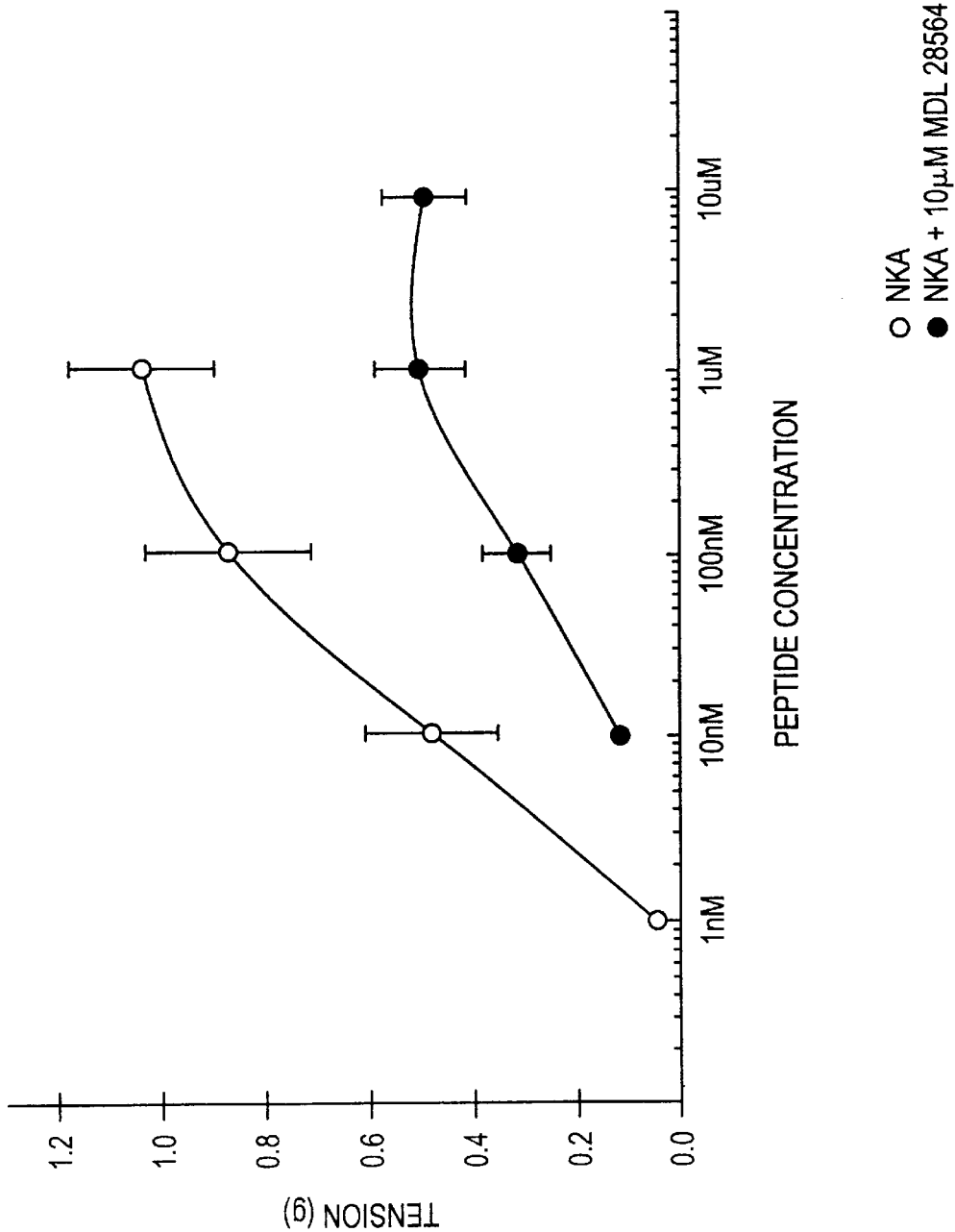

FIG. 4 illustrates the antagonistic effect of H-Asp-Ser-Phe-Val-Gly-LeuΨ(CH₂NH)Leu-NH₂(ID#2) on NKA-mediated contractile activity in hamster urinary bladder preparations (Example 3). The abscissa (x-axis) logarithmically indicates the concentration in nanomolar (nM) of NKA or NKA with 10 μM of H-Asp-Ser-Phe-Val-Gly-LeuΨ(CH₂NH)Leu-NH₂(ID#2). Values are MEAN±S.E.M. from one experiment in triplicate.

Figure 5:
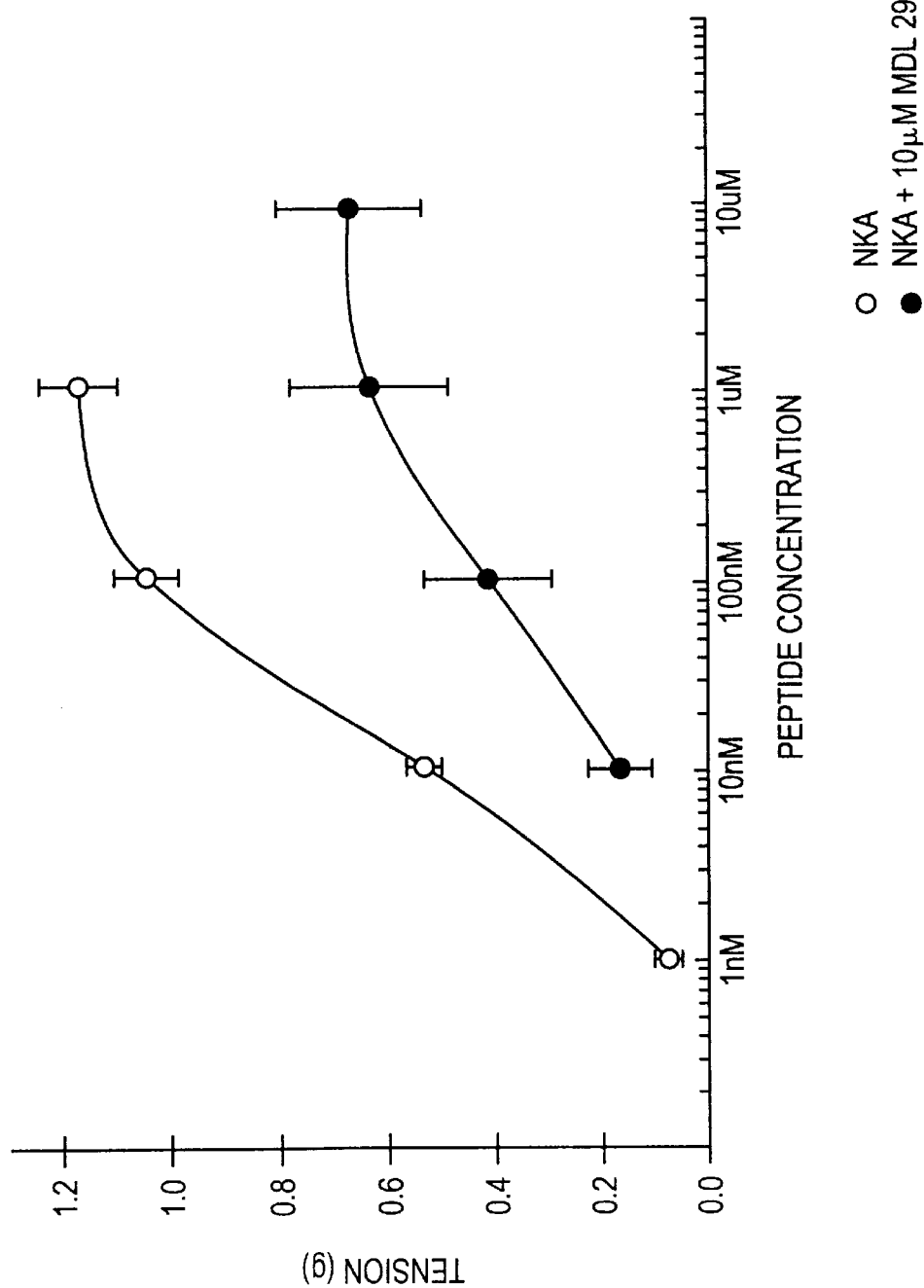

FIG. 5 illustrates the antagonistic effect of H-Asp-Ser-Phe-Val-Gly-LeuΨ(CH₂NH)Leu-NH₂(ID#2) on NKA-mediated contractile activity in hamster urinary bladder preparations (Example 3). The abscissa (x-axis) logarithmically indicates the concentration in nanomolar (nM) of NKA or NKA with 10 μM of H-Asp-Ser-Phe-Val-Gly-LeuΨ(CH₂NCH₃)Leu-NH₂(ID#3). Values are MEAN±S.E.M. from one experiment in triplicate.

DETAILED DESCRIPTION OF THE INVENTION

The following common abbreviations of the amino acids and amino and carboxy terminal groups are used throughout this specification:

Gly (or G)—glycine
Ala (or A)—alanine
Val (or V)—valine
Leu (or L)—leucine
Ile (or I)—isoleucine
Fum—fumaryl
Orn—ornithine
Pro (or P)—proline
Phe (or F)—phenylalanine
Trp (or W)—tryptophan
Met (or M)—methionine
Ser (or S)—serine
Thr (or T)—threonine
Cys (or C)—cysteine
Tyr (or Y)—tyrosine
Asn (or N)—asparagine
Gln (or Q)—glutamine
Asp (or D)—aspartic acid
Glu (or E)—glutamic acid
Lys (or K)—lysine
Arg (or R)—arginine
His (or H)—histidine
Nle—norleucine
Hyp—hydroxyproline
Glt—glutaryl
Mal—maleyl
Npa—β-(2-naphthyl)alanine
3,4-dehydroPro—3,4-dehydroproline
Pgl—phenylglycine
NMePgl—N-methyl-phenylglycine
Sar—sarcosine (N-methylglycine)
pSubPhe—para substituted phenylalanine
SubPhe—ortho, meta, or para, mono- or di-substituted phenylalanine
DAla (or a)—D-alanine
β-Ala—β-alanine
Ac—acetyl
Suc—succinyl
pClPhe—para-chloro-phenylalanine
pNO₂Phe—para-nitro-phenylalanine
NMeVal—N-methyl-valine An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. The alkylidene moiety of the phenyl-alkylidene groups of this invention can contain from 1 to 4 carbon atoms and may be straight or branched, for example, methylene, ethylene, propylene, butylene, isopropylidene, and sec-butylidene. The phenyl moiety of the phenylalkylidene groups of this invention can be unsubstituted or can be mono substituted at the ortho, meta, or preferably the para positions. Unsubstituted phenyl or para hydroxyphenyl are preferred. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo, or iodo group. In the X groups of this invention, the hydrogen, alkyl, or acyl moiety is attached to the alpha amino group of the amino terminal amino acid. Those peptides wherein the amino group of the amino terminal amino acid is substituted with two alkyl or acyl groups are also considered to be within the scope of the peptides of this invention.

It should be apparent that the peptide derivatives of this invention involve peptides wherein the normal peptide amide bond of the two carbon terminal amino acids of naturally occurring neurokinin A have been modified and these two modified amino acids are chemically depicted herein as the group Y. Utilizing conventional nomenclature employed by peptide chemists, the Y group which is comprised of two Leu residues (i.e., wherein $R_1$ and $R_2$ are each a sec-butyl group) having as their amide linkage modified by reducing the carbonyl group to a methylene group, can be designated as LeuΨ(CH₂NH)Leu. This designation indicates that the amide carbonyl group of the penultimate Leu is reduced to a methylene group. Other nomenclature designations used to describe the peptide derivatives of this invention are Ψ(CH₂S), Ψ(CH₂O), Ψ(CH=CH), Ψ(C(O)CH₂), Ψ(CH(OH)CH₂), and Ψ(NHC(O)), and Ψ(CH₂S(O)).

The term "a bond" when used in relation to the definition of $A_1$ is intended to mean that the X group is directly bonded to the $A_2$ group or in the instances where $A_2$ is also a bond, X is then directly bonded to the $A_3$ group. Likewise the term "a bond" when used in relation to the definition of $A_2$ is intended to mean that $A_1$ is directly bonded to the $A_3$ group or in the instances where $A_1$ is also a bond, X is then directly bonded to the $A_3$ group.

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are βalanine, norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenyl-butyric acid (Pba), phenylalanines substituted at the ortho, meta, or para position of the phenyl moiety with one or two of the following, a $(C_1-C_4)$ alkyl, $(C_1-C_4)$ alkoxy, halogen, or nitro groups or substituted with a methylenedioxy group, β-2- and 3-thienylalanine, β-2- and 3-furanylalanine, β-2-, 3-, and 4-pyridylalanine, β-(benzothienyl-2- and 3-yl) alanine, β-(1- and 2-naphthyl)alanine, O-alkylated derivatives of serine, threonine, or tyrosine, S-alkylated cysteine, the O-sulfate ester of tyrosine, 3,5-diiodo-tyrosine and the D-isomers of the naturally occurring amino acids.

The natural amino acids with the exception of glycine, contain a chiral carbon atom. Unless otherwise specifically indicated, the optically active amino acids, referred to herein, are of the L-configuration. As is customary, the structure of peptides written out herein is such that the amino terminal end is on the left side of the chain and the carboxy terminal end is on the right side of the chain. Consistent with this and with customary usage, the B groups are drawn such that the open valence on the left side is attached to the carbon atom of the Y group bearing an "H", the "$R_1$" group, and an "NH" group and the open valence on the right hand side of the B group is attached to the carbon atom of the Y group bearing an "H", the "$R_2$" group, and an "$CONH_2$".

Optionally for Y of structure 1, the B element of Y can be designated and incorporated into the structural features of Y. For example, a Y group of the formula

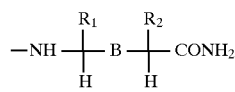

wherein B is a group of one of the formulae

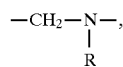

and can be optionally represented as Y of the formula

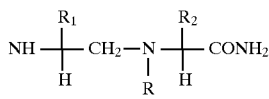

wherein for either designation R is a hydrogen atom or an alkyl group of from 1 to 5 carbon atoms, isovaleryl, or is a phenylalkylidene group wherein the alkylidene moiety is straight or branched and has from 1 to 6 carbon atoms and wherein the phenyl moiety is unsubstituted or is mono substituted with a $C_{1-4}$ alkyl, $C_{1-4}$ alkoxy, hydroxy, or halogen group; other substituents are as previously designated. The essential feature of the optional Y designation is to incorporate the B element as one of the structural features of the Y element.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

As with any generic group of chemical compounds, certain groups are preferred. Applicants prefer those peptide derivatives of formula 1 wherein X is a hydrogen and where $A_1$ is a bond, applicants prefer those peptide derivatives of formula 1 wherein X is Glt, Mal, Fum, and especially Suc. Applicants also prefer those peptide derivatives of formula 1 wherein $A_1$ is His-Lys-Thr, Lys-Thr, Thr, Asp-Val-Pro-Lys, Val-Pro-Lys-Ser, Pro-Lys-Ser, Lys-Ser, Ser, pGlu-Pro-Ser-Lys, Pro-Ser-Lys, Ser-Lys, or Lys. Applicants especially prefer those peptide derivatives of formula 1 wherein $A_1$ is His-Lys-Thr, Lys-Thr, or Thr. Applicants prefer those peptide derivatives of formula 1 wherein $A_2$ is Asp. Applicants also prefer those peptide derivatives of formula 1 wherein $A_3$ is Gly, Gln, Asn, Sar and especially Ala or Ser. Applicants further prefer those peptide derivatives of formula 1 wherein $A_4$ is Phe as well as those peptide derivatives of formula 1 wherein $A_5$ is Val and wherein $A_6$ is Gly. Applicants prefer those peptide derivatives of formula 1 wherein B is —$CH_2NH$— as well as those wherein $R_1$ is isobutyl, that is 2-(methylthio) ethyl, or benzyl and wherein $R_2$ is 2-methylthioethyl, benzyl, isobutyl, or n-butyl. Applicants especially prefer those compounds wherein $R_1$ and $R_2$ are each an isobutyl. The most preferred peptide derivatives of formula 1 are H-Asp-Ser-Phe-Val-Gly-LeuΨ($CH_2NH$)-Leu-$NH_2$(ID#2) wherein R is H or a methyl group. Further, most preferred peptide derivatives of formula 1 also include peptides of the following structures:

Asp-Ser-Phe-Val-Gly-Leu(Ψ($CH_2NH$))Met-$NH_2$; (ID#1)
Asp-Ser-Phe-Val-Gly-Leu(Ψ($CH_2NH$))Leu-$NH_2$; (ID#2)
Asp-Ser-Phe-Val-Gly-Leu(Ψ($CH_2NCH_3$))Leu-$NH_2$; (ID#3)
Asp-Ser-Phe-Val-Gly-Leu(Ψ($CH_2NCH_2CH_3$))Leu-$NH_2$; (ID#4)
Asp-Ser-Phe-Val-Gly-Leu(Ψ($CH_2N(CH_2)_2CH_3$))Leu-$NH_2$; (ID#5)
Asp-Ser-Phe-Val-β-Ala-Leu(Ψ($CH_2NH$))Leu-$NH_2$; (ID#14)
Asp-Ser-Phe-Val-Gly-Phe(Ψ($CH_2NH$))Leu-$NH_2$; (ID#15)
Asp-Ser-Phe-Val-Gly-Leu(Ψ($CH_2NH$))Phe-$NH_2$; (ID#16)
Asp-Ser-Phe-Val-Gly-Leu(Ψ($CH_2N(Iva)$))Leu-$NH_2$; (ID#17)

The proteins of this invention can be prepared by a variety of procedures readily known to those skilled in the art. Such procedures include the solid phase sequential procedure which can be performed using established automated methods such as by use of an automated peptide synthesizer. To prepare the peptide derivatives of this invention, a modified dipeptide corresponding to the carbon terminal dipeptide having the modified peptide linkage or its precursor is bound to a resin support. Procedures to be employed to prepare each of the modified peptide linkages are well known in the art and can be readily performed by skilled peptide chemists. The procedure to prepare those peptide derivatives of formula 1 wherein B is a —NHCO— group, that is the Ψ(NHCO) compounds, is known from Chorev and Goodman, *Int. J. Pept. Protein Res.*, 21(3), 258–68 (1983). The procedure to prepare those peptide derivatives of formula 1 wherein B is a —COCH$_2$— or —CH(OH)CH$_2$— group, that is the Ψ(COCH$_2$) and Ψ(CH(OH)CH$_2$) compounds, respectively, is known from Holladay and Rich, *Tetrahedron Letters*, 24(41), 4401–04, (1983). The procedure to prepare those peptide derivatives of formula 1 wherein B is a —CH$_2$NH— group, that is the Ψ(CH$_2$NH) compounds, is known from Sasaki and Coy, *Peptides*, Vol. 8, pp. 119–121, 1987 and is more fully described below. The procedure to prepare those peptide derivatives of formula 1 wherein B is a —CH$_2$S— group, that is the Ψ(CH$_2$S) compounds, is known from Spatola and Darlak, *Tetrahedron Letters*, 44(3), 821–33 (1988). The procedure to prepare those peptide derivatives of formula 1 wherein B is a —CH$_2$O— group, that is the Ψ(CH$_2$O) compounds, is known from TenBrink, *J. Org. Chem.*, 1987, 52, 418–22.

Specifically, the compounds of this invention wherein B is a —CH2N(R)— group are prepared by reducing the N-methoxy-N-methylamide of formula 3 to produce the aldehyde of formula 4.

ether phase with cold, dilute aqueous hydrochloric acid, drying and solvent removal. The crude product can be purified by, for example, column chromatography such as a silica gel column eluting with 55% ethyl/acetate/hexane.

The formula 4 aldehyde is then reacted with a resin-bound amino acid of formula 6

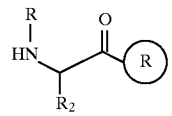

wherein R and R$_2$ are as defined for formula 1 and wherein Ⓡ represents the resin. The initially formed Schiff base adduct is reduced in situ, for example, by sodium cyanoborohydride, to give a resin bound modified dipeptide of formula 5

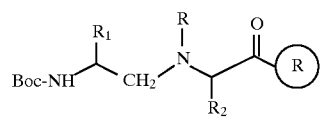

wherein R, R$_1$ and R$_2$ are as defined for formula 1 and wherein Ⓡ represents the resin.

Methods of reacting compounds of formula 4 with a amino acid of formula 6 on a resin support, through Schiff base formation and subsequent reduction to give modified dipeptides of formula 5, are preferred when R is hydrogen or methyl.

Alternative methods (Method B) of making the compounds of formula 5, wherein R is methyl, ethyl, propyl, isovaleryl, or like alkyl substituent of 1–5 carbon atoms, or Method A

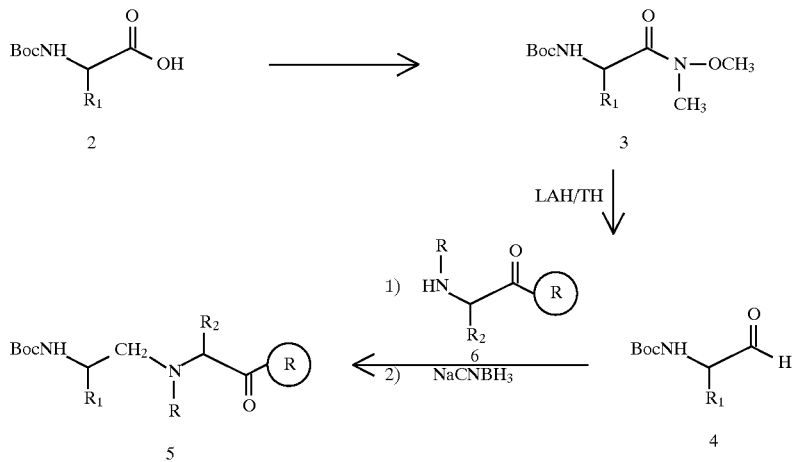

The reduction can be performed in any way generally known and readily performed by those skilled in the art such as by use of lithium aluminum hydride (LiAlH$_4$). This reduction can be conveniently carried out by adding about one molar equivalent of LiAlH$_4$ to a cooled, typically about 0° C., solution of a formula 2 compound in a nonreactive solvent such as an ethereal solvent such as tetrahydrofuran (THF) or diethylether. After the reaction is substantially complete, typically after about 30 minutes, the reaction mixture is quenched by the addition of, for example, 10% potassium or sodium hydrogen sulfate and then water. The product can then be isolated by, for example, extraction of the aqueous mixture with a solvent such as diethylether, washing the phenylalkylidene, can be performed by reductive alkylation. Specifically, compounds of

METHOD B

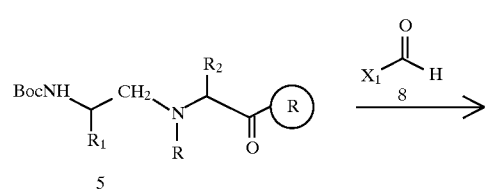

-continued
METHOD B

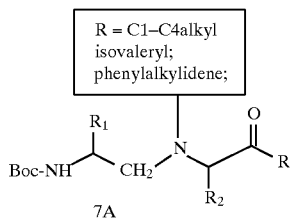

formula 5 wherein R is hydrogen can be subjected to a subsequent reaction with compounds of the formula 8 to produce the modified dipeptide of formula 7A, wherein the subsequent R group is derived from the substituted alkyl group of formula 8 (represented as $X_1$ and a functional aldehyde group).

The alternative method (method B) first reacts a formula 8 aldehyde with the resin bound dipeptide of formula 5, wherein R is a hydrogen group and the circled R represents the resin. The initially formed Schiff base adduct is then reduced in situ using, for example, sodium cyanoborohydride to give a resin bound dipeptide of formula 7A.

The $A_6$ through $A_1$ amino acids can then be sequentially added to the resin bound modified dipeptide in the usual manner.

The N-methoxy-N-methyl amides of formula 2 are prepared from the corresponding N-Boc protected acid in the usual manner. Carbonyldiimidazole is added to a dried solution of the N-Boc protected amino acid in an ethereal solvent such as diethylether. The reaction mixture is allowed to stir for from 10 minutes to 1 hour, typically for about 15–20 minutes. N,O-dimethylhydroxylamine HCl in DMF and a sterically hindered amine such as diisopropylethylamine is added and the mixture allowed to stir for from about 6 hours up to about 24 hours at room temperature. The desired compound is then isolated by solvent evaporation and crude purification can be accomplished by, for example, flash chromatography on silica gel eluting with methylene chloride.

The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., *Chem. Ind.* (*London*) 38, 1597–98 (1966). A chloromethylated resin is commercially available from Bio 30 Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxy-methylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific a-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethane type protecting groups such as benzyloxycarbonyl and substituted benzyloxycarbonyl, such as p-chlorobenzyloxycarbonyl, p-nitrobenzyloxycarbonyl, p-bromobenzyl-oxycarbonyl, p-methoxybenzyloxycarbonyl, 1-(p-biphenylyl)-1-methylethoxy-carbonyl, α, α-dimethyl-3,5-dimethoxybenzyloxycarbonyl and benzhydryloxycarbonyl; (3) aliphatic urethane protecting groups such as tert-butyloxycarbonyl (Boc), diisopropyl-methoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(y-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970). After the desired amino acid sequence has been obtained, the peptide is removed from the resin. This can be done by hydrolysis such as by treatment of the resin bound polypeptide with a solution of dimethyl sulfide, p-cresol and thiocresol in anhydrous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The carboxylic hydroxyl group of Aspartic acid and Glutamic acid can be protected with a benzyl or cyclohexyl group. The preferred protecting group is benzyl.

These groups can be removed by procedures well known in the art. Typically protecting group removal is done after the peptide chain synthesis is complete but the protecting groups can be removed at any other appropriate time.

The ability of the peptide derivatives of formula 1 to act as antagonists of neurokinin A can be demonstrated by the ability of such peptides to compete with iodinated neurokinin A for mammalian neurokinin A (NK2) receptors using the method of Buck, et al., Science 226: 987–989, 1984, by the ability of such compounds to stimulate or to inhibit neurokinin A-induced phosphatidylinositol turnover using the method of Bristow, et al., British J. Pharmacol. 90: 211–21, 1987, or to antagonize neurokinin A-induced smooth muscle contraction using the method of Dion, et al., Life Sciences 41: 2269–2278, 1987.

By virtue of the ability of the peptide derivatives of this invention to act as antagonists of neurokinin A, the compounds are useful as immunosuppressants and in the treatment of arthritis, asthma, pain, inflammation, tumor growth, gastrointestinal hypermotility, Huntington's disease, psychosis, neuritis, neuralgia, headache including migraine, hypertension, urinary incontinence, urticaria, carcinoid syndrome symptoms, influenza, and common cold. Effective doses, whether oral or parenteral, can be readily determined by those of ordinary skill in the art and are those doses which causes antagonism of the neurokinin A (NK2) receptor. For example, effective doses of the peptides of this invention could be from about 0.5 $\mu$g/kg to about 500 mg/kg of the patient body weight per day. The compounds are conveniently administered in unit dosage forms containing from about 1 mg to about 500 mg of the active compound and can be administered in from one to four or more unit dosage forms per day. The term "patient" used herein is taken to mean mammals such as primates, including humans, sheep, horses, cattle, pigs, dogs, cats, rats, and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

Example 1

ANTAGONISM OF THE NEUROKININ A RECEPTOR BY H-ASP-SER-PHE-VAL-GLY-LEU-Ψ(CH$_2$NH)-LEU-NH$_2$(ID#2) and H-ASP-SER-PHE-VAL-GLY-LEU-Ψ(CH$_2$N(CH$_3$))-LEU-NH$_2$(ID#3) AS DEMONSTRATED BY THE EFFECT ON PHOSPHATIDYLINOSITOL TURNOVER Urinary bladders from several hamsters were pooled, minced, and homogenized in 50 mM TRIS-HCl (pH 7.4) containing 120 mM NaCl and 5 mM KCl at 4° C. and centrifuged at 48,000×g for 15 minutes. The pellet was resuspended for 30 minutes in 50 mM TRIS-HCl (pH 7.4) containing 10 mM EDTA and 300 mM KCl at 4° C. The suspension was centrifuged as above and the pellet was washed two times in plain 50 mM TRIS-HCl (pH 7.4) and centrifuged similarly. The tissue was then resuspended in incubation buffer and an aliquot (approximately 3–5 mg tissue) was added to each assay tube to commence the assay. The assay tubes contained incubation buffer consisting of 50 mM TRIS-HCl (pH 7.4), 0.02% BSA, 40 $\mu$g/ml bacitracin, 4 $\mu$g/ml chymostatin, 4 $\mu$g/ml leupeptin, 2 mM MnCl$_2$, 0.1 nM $^{125}$iodohistidyl$^1$-neurokinin A (Amersham Corp.), and concentrations of the title compounds or standards ranging from 0.03 nM to 100 $\mu$M. The assay was allowed to proceed to equilibrium for 120 min at room temperature. After this time, the contents of each tube was rapidly filtered over Whatman GF/B filters presoaked in 0.5% BSA and the filters were rapidly washed two times with ice-cold plain 50 mM TRIS-HCl (pH 7.4). Filter-bound radioactivity was quantitated in a gamma counter. Specific binding (maximum) was defined as the difference between binding in the presence and absence of 1 $\mu$M unlabeled neurokinin A. Competition of iodinated neurokinin A binding by test compounds or standards was expressed as a percentage of this maximum competition. IC$_{50}$ values (concentration required to inhibit 50% of receptor binding) were found to be 100–200 nM for the title compounds.

Example 2

ANTAGONISM OF THE NEUROKININ A RECEPTOR BY H-ASP-SER-PHE-VAL-GLY-LEU-Ψ(CH$_2$NH)-LEU-NH$_2$(ID#2) and H-ASP-SER-PHE-VAL-GLY-LEU-Ψ(CH$_2$N(CH$_3$))-LEU-NH$_2$(ID#3) AS DEMONSTRATED BY THE EFFECT ON PHOSPHATIDYLINOSITOL TURNOVER

Urinary bladders from several hamsters were pooled and chopped at 350 µm with a tissue chopper. The chopped tissue was then incubated in 37° C. Krebs-Hepes buffer with fresh buffer changes every 15 minutes for 30 minutes. The tissue was then incubated in this buffer containing 100–200 µCi of $^3$H-inositol at 37° C. The tissue was then washed and incubated for another 30 minutes in Krebs-Hepes (containing 10 mM Li$^+$) at 37° C. with fresh buffer change every 15 minutes. Portions of the tissue mass (approximately 10–20 mg per assay tube) were then placed in Li$^+$ buffer, test compound was then added in 25 µl, and then various concentrations of neurokinin A were added in 25 µl in a final volume of 250 µl. Test compound was evaluated at concentrations ranging from 1 nM to 100 µM and neurokinin A concentrations ranged from 1 nM to 10 µM. Test compound was also evaluated alone at the indicated concentrations to test for agonist activity. After 30 minutes at room temperature, the phosphatidylinositol turnover was terminated by the addition of 940 µl chloroform:methanol (1:2), followed by 310 µl chloroform, followed by 310 µl water. Each tube was then vortexed for 15 seconds and then centrifuged at 3000 rpm for 10 minutes to separate the phases. 900 µl of the top (aqueous) phase was then loaded onto a 0.5 ml Biorad AG-1×8 (formate) ion exchange column. 50 µl of the bottom phase (chloroform) was withdrawn from each tube and placed in a counting vial, dried, and counted in scintillation fluid. The material on the columns was washed in order with:

1) 10 ml of water
2) 5 ml of 5 mM disodium tetraborate/60 mM sodium formate
3) 10 ml of 1M ammonium formate in 0.1M formic acid The final (third) wash was collected and one ml was mixed with 6 ml of ACS scintillant and counted. The ratio of these counts (total inositol phosphates) to the corresponding organic phase counts was then calculated for each sample. The ratios in the presence of test compound and/or standards were then compared to the ratios for control tubes (i.e., no stimulating agonist). Dose-response curves were constructed and the abilities of test compounds to stimulate or to inhibit neurokinin A-induced phosphatidylinositol turnover were determined by graphical analysis or with the aid of a computer program.

Example 3

HAMSTER URINARY BLADDER CONTRACTION PREPARATION

Half-strips of urinary bladders from male golden Syrian hamsters (75–100 g) were suspended in Tyrode's buffer at 31° C. and with 1 gram resting tension as described by Dion et al. (Life Sciences 41: 2269–2278, 1987). The enkephalinase inhibitor thiorphan was added to the buffer at 10 µM 15 minutes prior to each test compound addition. Cumulative NKA dose-response curves were constructed first in the absence and then in the presence of test compound. The test compounds were added cumulatively as well to ascertain whether or not they had any contractile effects themselves. Any test compound effect that was observed was allowed to plateau before the next cumulative concentration was added. Under these conditions, the EC$_{50}$ for NKA contractile effects was generally 10 nM, in good agreement with literature values. Contractile data are expressed as grams of tension developed over and above the resting tension. In three separate hamster bladder tissues each, H-Asp-Ser-Phe-Val-Gly-LeuΨ(CH$_2$NH)Leu-NH$_2$(ID#2) or H-Asp-Ser-Phe-Val-Gly-LeuΨ(CH$_2$N(CH$_3$))Leu-NH(ID#3) up to concentrations of 10 µM did 10 not produce any contraction.

Example 4

I. Boc-Leu-aldehyde synthesis (Fehrentz, J.-A. and Castro, B. *Synthesis*, 1983, 676–678):

A. N-t-Boc-Leucine N-methoxy-N-methylamide:

15.0 mmoles of Boc-Leucine hydrate was dissolved in 30 ml dry ether. The solution was dried over anhydrous MgSO$_4$ and the solid removed by filtration. 16.5 mmoles of carbonyldiimidazole was added to the filtrate and the reaction stirred 20 minutes at room temperature. To the resulting solution was added a suspension of 0,N-dimethylhydroxylamine hydrochloride (22.5 mmoles) in 15 ml dimethylformamide and 3.9 ml diisopropylethylamine. The reaction mixture was stirred overnight at room temperature. The reaction was diluted into ethyl acetate (75 ml) and washed with cold 1N HCl (3×40 ml), saturated NaHCO$_3$ (3×40 ml) and saturated NaCl (1×40 ml). The organic phase was dried with MgSO$_4$, filtered and the ethyl acetate removed in vacuo. Analytical Data: R$_f$(silica gel F254): 0.51 (ethyl acetate/hexane 3/2); $^1$H-NMR (CDCl$_3$) TMS int): δ=0.95 ppm (2d, 6H, J=6.6 Hz); 1.42 (s, 11H); 1.64–1.80 (m, 1H); 3.20 (s, 3H); 3.80 (s,3H); 4.72 (m, 1H); 5.10 (d, 1H, J=7.5 Hz). Mass Spec: M+H$^+$: Theoretical: 275. Observed: 275.

B. Boc-Leucine aldehyde;

2.5 mmoles of Boc-leucine N-methoxy-N-methylamide were dissolved in dry ether (30 ml). To this solution was added 3.2 mmole of lithium aluminum hydride (LiAlH$_4$ 1M solution in tetrahydrofuran). The reaction was stirred 20 minutes at room temperature and then carefully quenched by addition of a solution of NaHSO$_4$ (0.6 g) in 10 ml water. The reaction mixture was added to 75 ml ether and washed with cold 1N HCl (3×30 ml), saturated NaHCO$_3$ (3×30 ml) and saturated NaCl (1×30 ml). The organic phase was dried with MgSO$_4$, filtered and the solvent removed in vacuo. Analytical Data: Rf (silica gel 60 F254): 0.68 (ethyl acetate/hexane 3/2). Mass Spec: M=H$^+$: Theoretical: 216. Observed: 216.

II. Synthesis of Leu-Resin:

Standard solid phase peptide synthesis techniques on an automated peptide synthesizer were used. After formation of Boc-Leu-resin (0.5 mmoles), the Boc protecting group was removed and the resin washed with dimethylformamide, dichloromethane and dried. For example attachment of amino acids to a p-methyl-benzhydrylamine resin (p-Me-BHA) resin is well known in the art, e.g., Leu-p-Me-BHA resin.

III. Formation of reduced amide bond (LeuΨ(CH$_2$NH)):

The Boc-Leu aldehyde (2 mmoles) was dissolved in 1% acetic acid in dimethylformamide (10 ml) and this solution was added to the reaction vessel containing the Leu-resin (0.5 mmoles, see II. above). To this mixture was added a solution of NaCNBH$_3$ (150 mg) in 2 ml dimethylformamide. The mixture was shaken for 4 hours, the reaction vessel was drained and the resin washed with dimethylformamide, then dichloromethane.

IV. Synthesis of (Ψ(CH$_2$NH)$^9$, Leu$^{10}$)NKA$_{4-10}$: (ID#2)

The synthesis of the peptide was completed on the automated peptide synthesizer by sequential addition of the remaining amino acids (Gly, Val, Phe, Ser (Bzl) and Asp (Ch×1)). The peptide was cleaved from the resin and globally deprotected using anhydrous HF/anisole (10:1). The peptide was purified using reverse phase HPLC techniques.

Analytical Data: Amino Acid Analysis: (HCl digest) Asp (1.03); Ser (0.93); Gly (1.01); Val (0.96); Phe (0.74). Peptide Content: 53.4%. Fast Atom Bombardment Mass Spectrometry: M+H$^+$ Theoretical: 735. Observed: 735.

V. Synthesis of [Ψ(CH$_2$NCH$_3$)$^9$, Leu$^{10}$)NKA$_{4-10}$: (ID#3)

N-Methyl-Leu-resin (0.5 mmoles) (prepared from Boc-N-methyl Leucine according to II above) was reacted with 2.0 mmoles Boc-Leu aldehyde as described in III above. The peptide synthesis was then completed as described in IV above. Analytical Data: Amino Acid Analysis: (HCl digest) Asp (1.01); Ser (0.89); Gly (1.02); Val (1.00); Phe (0.98). Peptide Content: 53.5%. Fast Atom Bombardment Mass Spectrometry: M+H$^+$. Theoretical: 749. Observed: 749.

VI. Synthesis of (Ψ(CH$_2$NCH$_3$)$^9$, Leu$^{10}$)NKA$_{4-10}$: (ID#3) Asp-Ser-Phe-Val-Gly-Leu(Ψ(CH$_2$NCH$_3$))Leu-NH$_2$ The Boc-leucinal was prepared by initially forming the N-methoxy N-methyl amide as in example 4-IB. Essentially, the N-methoxy N-methyl amide (1.2 g, 4 mmol) is subsequently dissolved in dry THF (60 ml), chilled, and 1M LiAlH$_4$ in THF (5 ml) is added slowly. The reaction is allowed to come to room temperature while stirring the reaction for 30 minutes under nitrogen. The reaction is quenched with NaHSO$_4$ (1.2 g in 20 ml H$_2$O) and then further diluted with H$_2$O before extracting the product with ether (3×40 ml). The organic phase is dried over MgSO$_4$, filtered, and roto-evaporated to a white solid which was used directly in the next step.

The N-Me-Leu-pMe-BHA resin was prepared by coupling N-Me-Leucine to p-Me-BHA resin by standard procedures known in the art. The prepared resin is then reacted with the Boc-Leucinal as previously described in example 4-III. The synthesis of the peptide was completed by sequentially coupling each amino acid to the support using a automated peptide synthesizer. The final protected product on the resin was dried and characterized and isolated by cleaving the product from the resin and analyzing by HPLC. Subsequently, the final material was isolated by HPLC to yield 59.9 mg of product which was characterized: Analytical HPLC; Amino acid analysis (A882870A; 53.5% peptide); and by FABs-mass spectrophotometry (M882870A).

Alternatively(method B), Boc-Leu (Ψ(CH$_2$NH))-Leu resin is prepared according to steps II and III above. The resin is then reacted with 2.5 mmoles of formaldehyde (to form designated R group) in 10 ml of 1% HOAc in dimethylformamide in the presence of NaCNBH$_3$ as described in III above. The synthesis of the peptide is then completed as described in IV above.

VII. Synthesis of ID#15: Asp-Ser-Phe-Val-Gly-Phe(Ψ(CH$_2$NH))Leu-NH$_2$

The Boc-phenylalaninal was prepared by initially forming the N-methoxy N-methyl amide as in example 4-I. The N-methoxy N-methyl amide (1.2 g, 4 mmol) is subsequently dissolved in dry THF (60 ml), chilled, and 1M LiAlH$_4$ in THF (5 ml) is added slowly. The reaction is allowed to come to room temperature while stirring the reaction for 30 minutes under nitrogen. The reaction is quenched with NaHSO$_4$ (1.2 g in 20 ml H$_2$O) and then further diluted with H$_2$O before extracting the product with ether (3×40 ml). The organic phase is dried over MgSO$_4$, filtered, and roto-evaporated to a white solid which was used directly in the next step.

The Leu-pMe-BHA resin was prepared by coupling Leucine to a p-Me-BHA resin by standard procedures known in the art. The prepared resin is reacted with the Boc-phenylalaninal as previously described. The synthesis of the peptide was completed by sequentially coupling each amino acid to the support using a automated peptide synthesizer. The final protected product on the resin was dried and characterized and isolated by cleaving the product from the resin and analyzing by HPLC. By analytical HPLC the crude product appeared to be 60% pure. Subsequently final material was isolated by HPLC to yield 60.5 mg of product which was characterized by NMR (N893026); Amino acid analysis (A893026A; 62.6% peptide); and by FABs-mass spectrophotometry (M893026).

VII. Synthesis of ID#5: Asp-Ser-Phe-Val-Gly-Leu(Ψ(CH$_2$N(CH$_2$)$_2$CH$_3$))Leu-NH$_2$ The Leu-pMe-BHA resin was prepared by coupling Leucine to a p-Me-BHA resin by standard procedures known in the art. The prepared resin is reacted with the Boc-Lecinal as previously described in example 4-I,II,III.

The N-propyl group was then introduced to the resin bound dipeptide by reductive alkylation using n-propionaldehyde followed by reacting with sodium cyanoborohydride under standard procedures. Afterwards the resin was then washed with DMF, dichloromethane, and then air dried.

The synthesis of the peptide was completed by sequentially coupling each amino acid to the support using a automated peptide synthesizer. The final protected product on the resin was dried and characterized and isolated by cleaving the product from the resin and analyzing by HPLC. By analytical HPLC the crude product appeared to be 60% pure. Subsequently, the final material was isolated by HPLC to yield initially 39.4 mg of product. An additional 23 mg of product was isolated. The products where pooled and subsequently characterized: NMR (N893661); Amino acid analysis (A893661A; 65.1% peptide); and by FABs-mass spectrophotometry (M893661A).

IX. Synthesis of ID#17: Asp-Ser-Phe-Val-Gly-Leu(Ψ(CH2N(Iva))Leu-NH$_2$

The Leu-pMe-BHA resin was prepared by coupling Leucine to a p-Me-BHA resin by standard procedures known in the art. The prepared resin is reacted with the Boc-Lecinal as previously described in example 4-I,II,III.

The N-isovaleral group was then introduced to the dipeptide bound to the resin by reductive alkylation using the isovaleraldehyde dissolved in 1% acetic acid in DMF for 2 hours followed by reacting with sodium cyanoborohydride under standard procedures. Afterward the resin was then washed with DMF, dichloromethane, and then air dried.

The synthesis of the peptide was completed by sequentially coupling each amino acid to the support using a automated peptide synthesizer. The final protected product on the resin was dried and characterized and isolated by cleaving the product from the resin and analyzing by HPLC. Subsequently, the final material was isolated by HPLC to yield initially 52.0 mg of product. The products where pooled and subsequently characterized: Amino acid analysis (A901298B; 56.4% peptide); and by FABs-mass spectrophotometry (M901298A);

X. Synthesis of ID#16: Asp-Ser-Phe-Val-Gly-Leu(Ψ(CH$_2$NH))Phe-NH$_2$

The Phe-p-Me-BHA resin was prepared by coupling Phenylalanine to p-Me-BHA resin (0.5 mmol; 1.1 meg/g) by standard procedures known in the art. The prepared resin is reacted with the Boc-Lecinal as previously described in example 4-I,II,III.

The synthesis of the peptide was completed by sequentially coupling each amino acid to the support using a automated peptide synthesizer. The final protected product on the resin was dried and characterized and isolated by cleaving the product from the resin and analyzing by HPLC. Subsequently final material was isolated by HPLC to yield initially 27.4 mg of product. The products where pooled and subsequently characterized: Amino acid analysis (A901385B; 60.9% peptide); and by FABs-mass spectrophotometry (M901385A);

XI. Synthesis of ID#1: Asp-Ser-Phe-Val-Gly-Leu(Ψ(CH$_2$NH))Met-NH$_2$

The Met-p-Me-BHA resin was prepared by coupling Boc-methionine to p-Me-BHA resin (0.5 mmol; 1.1 meg/g)

by standard procedures known in the art. The prepared resin is reacted with the Boc-Lecinal as previously described in example 4-I,II,III.

The synthesis of the peptide was completed by sequentially coupling each amino acid to the support using a automated peptide synthesizer. The final protected product on the resin was dried and characterized and isolated by cleaving the product from the resin and analyzing by HPLC. Subsequently final material was isolated by HPLC to yield initially 15.8 mg of product Impurities present were removed by another round of HPLC chromatography to give 11.1 mg: Amino acid analysis (A882319A; 50.6%% peptide); and by FABs-mass spectrophotometry (M882319A);

| PEPTIDES MADE BY PROCEDURES DESCRIBED ABOVE | | |
|---|---|---|
| ID #1 | Asp—Ser—Phe—Val—Gly—Leu(ψ(CH$_2$NH))Met—NH$_2$ | MDL29,646 |
| ID #2 | Asp—Ser—Phe—Val—Gly—Leu(ψCH$_2$NH))Leu—NH$_2$ | MDL28,564 |
| ID #3 | Asp—Ser—Phe—Val—Gly—Leu(ψ(CH$_2$NCH$_3$))Leu—NH$_2$ | MDL29,916 |
| ID #4 | Asp—Ser—Phe—Val—Gly—Leu(ψCH$_2$NCH$_2$CH$_3$))Leu—NH$_2$ | MDL29,716 |
| ID #5 | Asp—Ser—Phe—Val—Gly—Leu(ψ(CH$_2$N(CH$_2$)$_2$CH$_3$))Leu—NH$_2$ | MDL102,863 |
| ID #14 | Asp—Ser—Phe—Val-β-Gly—Ala—Leu(ψ(CH$_2$NH))Leu—NH$_2$ | MDL102,500 |
| ID #15 | Asp—Ser—Phe—Val—Gly—Phe(ψ(CH$_2$NH))Leu—NH$_2$ | MDL102,056 |
| ID #16 | Asp—Ser—Phe—Val—Gly—Leu(ψ(CH$_2$NH))Phe—NH$_2$ | MDL101,382 |
| ID #17 | Asp—Ser—Phe—Val—Gly—Leu(ψ(CH$_2$N(Iva))Leu—NH$_2$ | MDL101,608 |

Table 1, SYNTHETIC PEPTIDES AND THEIR ACTIVITIES, gives measured values of (CH2NR) peptides to antagonize binding at the NKA receptor as demonstrated by the ability of test compounds to displace $I^{125}$ labeled NKA from hamster urinary bladder (NK-2 column) (See Example 3). Values given indicate the concentration in nanomoles of antagonist to reach the IC50 of the neurokinin A (NKA) receptor. SKLKB82#3 represents a cloned NK-2 receptor cell line; the sample is prepared from the scraped cell pellet for assay as earlier described for the hamster urinary bladder preparations. NK-1 represents a substance P receptor preparation from rat salivary gland; receptors are prepared as earlier described for the hamster urinary bladder preparations. Blank spaces indicate compound has not been tested in that particular assay.

TABLE 1

SYNTHETIC PEPTIDES AND THEIR ACTIVITIES

| [ψ(CH$_2$NR)] Peptides | MDL # | Hamster Urinary Bladder NK-2 IC$_{50}$ (nM) | SKLKB82#3 IC$_{50}$ (nM) | NK-1 IC$_{50}$ (nM) |
|---|---|---|---|---|
| Asp—Ser—Phe—Val—Gly—Leu[ψ(CH$_2$NH)]Met—NH$_2$ (ID #1) | 29,646 | 50 ± 5 | | >10 × 10$^3$ |
| Asp—Ser—Phe—Val—Gly—Leu[ψ(CH$_2$NH)]Leu—NH$_2$ (ID #2) | 28,564 | 157 ± 17 | | >10 × 10$^5$ |
| Asp—Ser—Phe—Val—Gly—Leu[ψ(CH$_2$NCH$_3$)]Leu—NH$_2$ (ID #3) | 29,916 | 210 ± 15 | | |
| Asp—Ser—Phe—Val—Gly—Leu[ψ(CH$_2$NCH$_2$CH$_3$))Leu—NH$_2$ (ID #4) | 29,716 | 257 ± 30 | 4733 ± 393 | |
| Asp—Ser—Phe—Val—Gly—Leu[ψ(CH$_2$N(CH$_2$)$_2$CH$_3$)]Leu—NH$_2$ (ID #5) | 102,863 | 103 ± 13 | | |
| Asp—Ser—Phe—Val—Gly[ψCH$_2$NH)]Leu—Leu—NH$_2$ (ID #6) | 102,423 | >10 × 10$^3$ | | |
| Asp—Ser—Phe—Val—Gly[ψCH$_2$NCH$_3$)]Leu—Leu—NH$_2$ (ID #7) | 102,369 | >10 × 10$^3$ | | |
| Asp—Ser—Phe—Val[ψ(CH$_2$NH)]Gly—Leu—Leu—NH$_2$ (ID #8) | 29,882 | >5 × 10$^3$ | | >10 × 10$^4$ |
| Asp—Ser—Phe—Val[ψ(CH$_2$NCH$_3$)]Gly—Leu—Leu—NH$_2$ (ID #9) | 29,712 | >5 × 10$^3$ | | |
| Asp—Ser—Phe[ψ(CH$_2$NH)]Val—Gly—Leu—Leu—NH$_2$ (ID #10) | 29,614 | >10 × 10$^3$ | | |
| Asp—Ser—Phe[ψ(CH$_2$NCH$_3$)]Val—Gly—Leu—Leu—NH$_2$ (ID #11) | 29,678 | >10 × 10$^3$ | | |
| Asp—Ser[ψ(CH$_2$NH)]Phe—Val—Gly—Leu—Leu—NH$_2$ (ID #12) | 29,883 | >10 × 10$^3$ | | |
| Suc[ψ(CH$_2$NH)]Ser—Phe—Val—Gly—Leu—Leu—NH$_2$ (ID #13) | 101,905 | 2 × 10$^3$ | | |
| Asp—Ser—Phe—Val-β-Ala—Leu[ψ(CH$_2$NH)]Leu—NH$_2$ (ID #14) | 102,500 | 19 ± 3 | | |
| Asp—Ser—Phe—Val—Gly—Phe[ψ(CH$_2$NH)]Leu—NH$_2$ (ID #15) | 102,056 | >10 × 10$^3$ | | |
| Asp—Ser—Phe—Val—Gly—Leu[ψ(CH$_2$NH)]Phe—NH$_2$ (ID #16) | 101,382 | 5 | 200 | |
| Asp—Ser—Phe—Val—Gly—Leu[ψ(CH$_2$N(Iva)]Leu—NH$_2$ (ID #17) | 101,608 | 175 | 3000 | |
| Asp—Ser—Phe—Val—Gly—Leu[ψ(CH$_2$NH)]Leu—CH$_2$OH (ID #18) | 102,678 | >10 × 10$^3$ | >10 × 10$^3$ | |

What is claimed is:

1. A peptide derivative of the formula $$X—A_1—A_2—A_3—A_4—A_5—A_6—Y$$

wherein X is hydrogen, an alkyl group of from 1 to 6 carbon atoms, or an acyl group of from 2 to 10 carbon atoms;

$A_1$ is a bond;
$A_2$ is Asp;
$A_3$ is Ser;
$A_4$ is Phe;
$A_5$ is Val;
$A_6$ is Gly or B-Ala;
Y is a group of the formula $$NH-\underset{H}{\overset{R_1}{C}}-CH_2-\underset{R}{N}-\underset{H}{\overset{R_2}{C}}-R_3 \quad a)$$

wherein R is a hydrogen atom or an alkyl group of from 1 to 5 carbon atoms or isovaleryl;

$R_1$ and $R_2$ are each independently selected from isobutyl, benzyl, and 2-(methylthio)ethyl groups;

$R_3$ is —CONH; or
said peptide is a pharmaceutically acceptable salt thereof.

2. A peptide derivative of the formula of claim 1 having the following sequence:

Asp-Ser-Phe-Val-Gly-Leu($\Psi$(CH$_2$NH))Met-NH$_2$(ID#1).

3. A peptide derivative of the formula of claim 1 having the following sequence:

Asp-Ser-Phe-Val-Gly-Leu($\Psi$(CH$_2$NH))Leu-NH$_2$(ID#2).

4. A peptide derivative of the formula of claim 1 having the following sequence:

Asp-Ser-Phe-Val-Gly-Leu($\Psi$(CH$_2$NCH$_3$))Leu-NH$_2$ (ID#3).

5. A peptide derivative of the formula of claim 1 having the following sequence:

Asp-Ser-Phe-Val-Gly-Leu($\Psi$(CH$_2$NCH$_2$CH$_3$))Leu-NH$_2$ (ID#4).

6. A peptide derivative of the formula of claim 1 having the following sequence:

Asp-Ser-Phe-Val-Gly-Leu($\Psi$(CH$_2$N(CH$_2$)$_2$CH$_3$))Leu-NH$_2$(ID#5).

7. A peptide derivative of the formula of claim 1 having the following sequence:

Asp-Ser-Phe-Val-Gly-Phe($\Psi$(CH$_2$NH))Leu-NH$_2$(ID#15).

8. A peptide derivative of the formula of claim 1 having the following sequence:

Asp-Ser-Phe-Val-Gly-Leu($\Psi$(CH$_2$NH))Phe-NH$_2$(ID#16).

9. A peptide derivative of the formula of claim 1 having the following sequence:

Asp-Ser-Phe-Val-Gly-Leu($\Psi$(CH$_2$N(Iva))Leu-NH$_2$ (ID#17).

10. A peptide derivative of the formula of claim 1 wherein R is hydrogen.

11. A peptide derivative of the formula of claim 1 wherein R is methyl.

12. A peptide derivative of the formula of claim 1 wherein R is ethyl.

13. A peptide derivative of the formula of claim 1 wherein R is propyl.

14. A peptide derivative of the formula of claim 1 wherein R is isovaleryl.

15. A method of treating asthma in a patient in need there of comprising administering to the patient an effective amount of a peptide derivative of the formula of one of claims 2, 14, 1.

16. A pharmaceutical composition containing a compound of one of claims 2–14 or 1.

17. A peptide having the sequence:

Asp-Ser-Phe-Val-$\beta$-Ala-Leu($\Psi$(CH$_2$NH))Leu-NH$_2$ (ID#14).

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Xaa is a Leucine analog
            having a 1- methylene group, in place of a
            1-carbonyl group, bonded to the alpha nitrogen of ( i x ) FEATURE:
        ( A ) NAME/KEY: Modified-site
        ( B ) LOCATION: 6
        ( D ) OTHER INFORMATION: /note= "(cont'd) the subsequent
            amino acid"

( i x ) FEATURE:
        ( A ) NAME/KEY: Modified-site
        ( B ) LOCATION: 7
        ( D ) OTHER INFORMATION: /note= "Xaa is Methionin-1-amide
        ( M e t - N H 2 )"

( x i ) SEQUENCE DESCRIPTION: SEQ ID NO:1:

Asp  Ser  Phe  Val  Gly  Xaa  Xaa
    1                      5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Xaa is a Leucine analog
            having a 1- methylene group, in place of a
            1-carbonyl group, bonded to the alpha nitrogen"

( i x ) FEATURE:
        ( A ) NAME/KEY: Modified-site
        ( B ) LOCATION: 6
        ( D ) OTHER INFORMATION: /note= "(cont'd) of the subsequent
            amino acid"

( i x ) FEATURE:
        ( A ) NAME/KEY: Modified-site
        ( B ) LOCATION: 7
        ( D ) OTHER INFORMATION: /note= "Xaa is Leucin-1-amide
        ( L e u - N H 2 )"

( x i ) SEQUENCE DESCRIPTION: SEQ ID NO:2:

Asp  Ser  Phe  Val  Gly  Xaa  Xaa
    1                      5

( 2 ) INFORMATION FOR SEQ ID NO:3:

( i ) SEQUENCE CHARACTERISTICS:
        ( A ) LENGTH: 7 amino acids (B) TYPE: amino acid
(D) TOPOLOGY: linear (ii) MOLECULE TYPE: peptide (ix) FEATURE:
 (A) NAME/KEY: Modified-site
 (B) LOCATION: 6
 (D) OTHER INFORMATION: /note= "Xaa is a Leucine analog having a 1- methylene group, in place of a 1-carbonyl group, bonded to the alpha nitrogen"

(ix) FEATURE:
 (A) NAME/KEY: Modified-site
 (B) LOCATION: 6
 (D) OTHER INFORMATION: /note= "(cont'd) of the subsequent amino acid"

(ix) FEATURE:
 (A) NAME/KEY: Modified-site
 (B) LOCATION: 7
 (D) OTHER INFORMATION: /note= "Xaa is N-methyl- Leucin-1-amide having a methyl bonded to the alpha nitrogen and said alpha nitrogen is (ix) FEATURE:
 (A) NAME/KEY: Modified-site
 (B) LOCATION: 7
 (D) OTHER INFORMATION: /note= "(cont'd) correspondingly bonded to the preceding amino acid"

(xi) SEQUENCE DESCRIPTION: SEQ ID NO:3:

Asp Ser Phe Val Gly Xaa Xaa
1       5

(2) INFORMATION FOR SEQ ID NO:4:

(i) SEQUENCE CHARACTERISTICS:
  (A) LENGTH: 7 amino acids
  (B) TYPE: amino acid
  (D) TOPOLOGY: linear (ii) MOLECULE TYPE: peptide (ix) FEATURE:
 (A) NAME/KEY: Modified-site
 (B) LOCATION: 6
 (D) OTHER INFORMATION: /note= "Xaa is a Leucine analog having a 1- methylene group, in place of a 1-carbonyl group, bonded to the alpha nitrogen"

(ix) FEATURE:
 (A) NAME/KEY: Modified-site
 (B) LOCATION: 6
 (D) OTHER INFORMATION: /note= "(cont'd) of the subsequent amino acid"

(ix) FEATURE:
 (A) NAME/KEY: Modified-site
 (B) LOCATION: 7
 (D) OTHER INFORMATION: /note= "Xaa is N-ethyl- Leucin-1-amide having a ethyl bonded to the alpha nitrogen and said alpha nitrogen is (ix) FEATURE:
 (A) NAME/KEY: Modified-site
 (B) LOCATION: 7
 (D) OTHER INFORMATION: /note= "(cont'd) bonded to the preceding numbered amino acid"

(xi) SEQUENCE DESCRIPTION: SEQ ID NO:4:

Asp Ser Phe Val Gly Xaa Xaa
1       5

(2) INFORMATION FOR SEQ ID NO:5:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 6
    ( D ) OTHER INFORMATION: /note= "Xaa is a Leucine analog
        having a 1- methylene group, in place of a
        1-carbonyl group, bonded to the alpha nitrogen"

( i x ) FEATURE:
    ( A ) NAME/KEY: Active-site
    ( B ) LOCATION: 6
    ( D ) OTHER INFORMATION: /note= "(cont'd) of the subsequent
        amino acid"

( i x ) FEATURE:
    ( A ) NAME/KEY: Modified-site
    ( B ) LOCATION: 7
    ( D ) OTHER INFORMATION: /note= "Xaa is
        N-propyl- Leucin-1-amide having a propyl bonded to
        the alpha nitrogen and said alpha nitrogen is ( i x ) FEATURE:
    ( A ) NAME/KEY: Modified-site
    ( B ) LOCATION: 7
    ( D ) OTHER INFORMATION: /note= "(cont'd) correspondingly
        bonded to the preceding numbered amino acid"

( x i ) SEQUENCE DESCRIPTION: SEQ ID NO:5:

Asp  Ser  Phe  Val  Gly  Xaa  Xaa
1                   5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /note= "Xaa is a Glycine analog
            having a 1- methylene group, in place of a
            1-carbonyl group, bonded to the alpha nitrogen"

( i x ) FEATURE:
        ( A ) NAME/KEY: Modified-site
        ( B ) LOCATION: 5
        ( D ) OTHER INFORMATION: /note= "(cont'd) of the subsequent
            amino acid"

( i x ) FEATURE:
        ( A ) NAME/KEY: Modified-site
        ( B ) LOCATION: 7
        ( D ) OTHER INFORMATION: /note= "Xaa is Leucin-1-amide
            ( L e u - N H 2 )"

( x i ) SEQUENCE DESCRIPTION: SEQ ID NO:6:

Asp  Ser  Phe  Val  Xaa  Leu  Xaa
1                   5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear (ii) MOLECULE TYPE: peptide (ix) FEATURE:
(A) NAME/KEY: Modified-site
(B) LOCATION: 5
(D) OTHER INFORMATION: /note= "Xaa is a Glycine analog having a 1- methylene group, in place of a 1-carbonyl group, bonded to the alpha nitrogen"

(ix) FEATURE:
(A) NAME/KEY: Modified-site
(B) LOCATION: 5
(D) OTHER INFORMATION: /note= "(cont'd) of the subsequent amino acid"

(ix) FEATURE:
(A) NAME/KEY: Modified-site
(B) LOCATION: 6
(D) OTHER INFORMATION: /note= "Xaa is N-methyl-Leucine having a methyl bonded to the alpha nitrogen and said alpha nitrogen is correspondingly"

(ix) FEATURE:
(A) NAME/KEY: Modified-site
(B) LOCATION: 6
(D) OTHER INFORMATION: /note= "(cont'd) bonded to the preceding numbered amino acid"

(ix) FEATURE:
(A) NAME/KEY: Modified-site
(B) LOCATION: 7
(D) OTHER INFORMATION: /note= "Xaa is Leucin-1-amide (Leu-NH2)"

(xi) SEQUENCE DESCRIPTION: SEQ ID NO:7:

Asp Ser Phe Val Xaa Xaa Xaa
1               5

(2) INFORMATION FOR SEQ ID NO:8:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: Modified-site
(B) LOCATION: 4
(D) OTHER INFORMATION: /note= "Xaa is a Valine analog having a 1- methylene group, in place of a 1-carbonyl group, bonded to the alpha nitrogen"

(ix) FEATURE:
(A) NAME/KEY: Modified-site
(B) LOCATION: 4
(D) OTHER INFORMATION: /note= "(cont'd) of the subsequent amino acid"

(ix) FEATURE:
(A) NAME/KEY: Modified-site
(B) LOCATION: 7
(D) OTHER INFORMATION: /note= "Xaa is Leucin-1-amide (Leu-NH2)"

(xi) SEQUENCE DESCRIPTION: SEQ ID NO:8:

Asp Ser Phe Xaa Gly Leu Xaa
1               5

(2) INFORMATION FOR SEQ ID NO:9:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
    (A) NAME/KEY: Modified-site
    (B) LOCATION: 4
    (D) OTHER INFORMATION: /note= "Xaa is Valine analog having
        a 1- methylene group, in place of a 1-carbonyl
        group, bonded to the alpha nitrogen"

(ix) FEATURE:
    (A) NAME/KEY: Modified-site
    (B) LOCATION: 4
    (D) OTHER INFORMATION: /note= "(cont'd) of the subsequent
        amino acid"

(ix) FEATURE:
    (A) NAME/KEY: Modified-site
    (B) LOCATION: 5
    (D) OTHER INFORMATION: /note= "Xaa is N-methyl-Glycine
        having a methyl bonded to the alpha nitrogen and
        said alpha nitrogen is correspondingly"

(ix) FEATURE:
    (A) NAME/KEY: Modified-site
    (B) LOCATION: 5
    (D) OTHER INFORMATION: /note= "(cont'd) bonded to the
        preceding numbered amino acid"

(ix) FEATURE:
    (A) NAME/KEY: Modified-site
    (B) LOCATION: 7
    (D) OTHER INFORMATION: /note= "Xaa is Leucin-1-amide
    (Leu-NH2)"

(xi) SEQUENCE DESCRIPTION: SEQ ID NO:9:

Asp Ser Phe Xaa Xaa Leu Xaa
1                5

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Xaa is a Phenylalanine
            analog having a 1-methylene group, in place of a
            1-carbonyl group, bonded to the alpha"

(ix) FEATURE:
        (A) NAME/KEY: Modified-site
        (B) LOCATION: 3
        (D) OTHER INFORMATION: /note= "(cont'd) nitrogen of the
            subsequent amino acid"

(ix) FEATURE:
        (A) NAME/KEY: Modified-site
        (B) LOCATION: 7
        (D) OTHER INFORMATION: /note= "Xaa is Leucin-1-amide
        (Leu-NH2)"

(xi) SEQUENCE DESCRIPTION: SEQ ID NO:10:

Asp Ser Xaa Val Gly Leu Xaa
1                5

(2) INFORMATION FOR SEQ ID NO:11:

(i) SEQUENCE CHARACTERISTICS:
        (A) LENGTH: 7 amino acids
        (B) TYPE: amino acid (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /note= "Xaa is a Phenylalanine analog having 1-methylene group, in place of a 1-carbonyl group, bonded to the alpha"

(ix) FEATURE:
    (A) NAME/KEY: Modified-site
    (B) LOCATION: 3
    (D) OTHER INFORMATION: /note= "(cont'd) nitrogen of the subsequent amino acid"

(ix) FEATURE:
    (A) NAME/KEY: Modified-site
    (B) LOCATION: 4
    (D) OTHER INFORMATION: /note= "Xaa is N-methyl-Valine having a methyl bonded to the alpha nitrogen and said alpha nitrogen is correspondingly"

(ix) FEATURE:
    (A) NAME/KEY: Modified-site
    (B) LOCATION: 4
    (D) OTHER INFORMATION: /note= "(cont'd) bonded to the preceding amino acid"

(ix) FEATURE:
    (A) NAME/KEY: Modified-site
    (B) LOCATION: 7
    (D) OTHER INFORMATION: /note= "Xaa is Leucin-1-amide (Leu-NH2)"

(xi) SEQUENCE DESCRIPTION: SEQ ID NO:11:

Asp Ser Xaa Xaa Gly Leu Xaa
1                   5

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is a Serine analog having a 1- methylene group, in place of a 1-carbonyl group, bonded to the alpha nitrogen"

(ix) FEATURE:
        (A) NAME/KEY: Active-site
        (B) LOCATION: 2
        (D) OTHER INFORMATION: /note= "(cont'd) of the subsequent amino acid"

(ix) FEATURE:
        (A) NAME/KEY: Modified-site
        (B) LOCATION: 7
        (D) OTHER INFORMATION: /note= "Xaa is Leucin-1-amide (Leu-NH2)"

(xi) SEQUENCE DESCRIPTION: SEQ ID NO:12:

Asp Xaa Phe Val Gly Leu Xaa
1                   5

(2) INFORMATION FOR SEQ ID NO:13:

(i) SEQUENCE CHARACTERISTICS:
        (A) LENGTH: 6 amino acids (B) TYPE: amino acid
                    (D) TOPOLOGY: linear (i i) MOLECULE TYPE: peptide (i x) FEATURE:
                    (A) NAME/KEY: Modified-site
                    (B) LOCATION: 1
                    (D) OTHER INFORMATION: /note= "Xaa is methylene replaces
                            carbonyl of Succinyl bondeded to the alpha
                            nitrogen of Serine"

(i x) FEATURE:
                    (A) NAME/KEY: Modified-site
                    (B) LOCATION: 6
                    (D) OTHER INFORMATION: /note= "Xaa is Leucin-1-amide
                            (Leu-NH2)"

(x i) SEQUENCE DESCRIPTION: SEQ ID NO:13:

Xaa    Phe    Val    Gly    Leu    Xaa
          1                           5

(2) INFORMATION FOR SEQ ID NO:14:

(i) SEQUENCE CHARACTERISTICS:
                    (A) LENGTH: 7 amino acids
                    (B) TYPE: amino acid
                    (D) TOPOLOGY: linear (i i) MOLECULE TYPE: peptide (i x) FEATURE:
                    (A) NAME/KEY: Modified-site
                    (B) LOCATION: 5
                    (D) OTHER INFORMATION: /note= "Xaa is beta-alanine"

(i x) FEATURE:
                    (A) NAME/KEY: Modified-site
                    (B) LOCATION: 6
                    (D) OTHER INFORMATION: /note= "Xaa is a Leucine analog
                            having a 1- methylene group, in place of a
                            1-carbonyl group, bonded to the alpha nitrogen"

(i x) FEATURE:
                    (A) NAME/KEY: Active-site
                    (B) LOCATION: 6
                    (D) OTHER INFORMATION: /note= "(cont'd) of the subsequent
                            amino acid"

(i x) FEATURE:
                    (A) NAME/KEY: Modified-site
                    (B) LOCATION: 7
                    (D) OTHER INFORMATION: /note= "Xaa is Leucin-1-amide
                            (Leu-NH2)"

(x i) SEQUENCE DESCRIPTION: SEQ ID NO:14:

Asp    Ser    Phe    Val    Xaa    Xaa    Xaa
          1                           5

(2) INFORMATION FOR SEQ ID NO:15:

(i) SEQUENCE CHARACTERISTICS:
                    (A) LENGTH: 7 amino acids
                    (B) TYPE: amino acid
                    (D) TOPOLOGY: linear (i i) MOLECULE TYPE: peptide (i x) FEATURE:
                    (A) NAME/KEY: Modified-site
                    (B) LOCATION: 6
                    (D) OTHER INFORMATION: /note= "Xaa is Phenylalanine analog
                            having a 1- methylene group, in place of a
                            1-carbonyl group, bonded to the alpha"

(i x) FEATURE:

(A) NAME/KEY: Modified-site
(B) LOCATION: 6
(D) OTHER INFORMATION: /note= "(cont'd) nitrogen of the
    subsequent amino acid"

(ix) FEATURE:
(A) NAME/KEY: Modified-site
(B) LOCATION: 7
(D) OTHER INFORMATION: /note= "Xaa is Leucin-1-amide
(Leu-NH2)"

(xi) SEQUENCE DESCRIPTION: SEQ ID NO:15:

Asp Ser Phe Val Gly Xaa Xaa
1               5

(2) INFORMATION FOR SEQ ID NO:16:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: Modified-site
(B) LOCATION: 6
(D) OTHER INFORMATION: /note= "Xaa is a Leucine analog
    having a 1- methylene group, in place of a
    1-carbonyl group, bonded to the alpha nitrogen"

(ix) FEATURE:
(A) NAME/KEY: Modified-site
(B) LOCATION: 6
(D) OTHER INFORMATION: /note= "(cont'd) of the subsequent
    amino acid"

(ix) FEATURE:
(A) NAME/KEY: Modified-site
(B) LOCATION: 7
(D) OTHER INFORMATION: /note= "Xaa is Phenylalanin-1-amide
(Phe-NH2)"

(xi) SEQUENCE DESCRIPTION: SEQ ID NO:16:

Asp Ser Phe Val Gly Xaa Xaa
1               5

(2) INFORMATION FOR SEQ ID NO:17:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: Modified-site
(B) LOCATION: 6
(D) OTHER INFORMATION: /note= "Xaa is a Leucine analog
    having a 1- methylene group, in place of a
    1-carbonyl group, bonded to the alpha nitrogen"

(ix) FEATURE:
(A) NAME/KEY: Modified-site
(B) LOCATION: 6
(D) OTHER INFORMATION: /note= "(cont'd) of the subsequent
    amino acid"

(ix) FEATURE:
(A) NAME/KEY: Modified-site
(B) LOCATION: 7
(D) OTHER INFORMATION: /note= "Xaa is
    N-isovaleryl- Leucin-1-amide having a isovaleryl
    group bonded to the alpha nitrogen and said alpha (ix) FEATURE:
   (A) NAME/KEY: Modified-site
   (B) LOCATION: 7
   (D) OTHER INFORMATION: /note= "(cont'd) nitrogen is correspondingly bonded to the preceding numbered amino acid"

(xi) SEQUENCE DESCRIPTION: SEQ ID NO:17:

Asp Ser Phe Val Gly Xaa Xaa
1               5

(2) INFORMATION FOR SEQ ID NO:18:

(i) SEQUENCE CHARACTERISTICS:
   (A) LENGTH: 7 amino acids
   (B) TYPE: amino acid
   (D) TOPOLOGY: linear (ii) MOLECULE TYPE: peptide (ix) FEATURE:
   (A) NAME/KEY: Modified-site
   (B) LOCATION: 6
   (D) OTHER INFORMATION: /note= "Xaa is Leucine analog having a 1- methylene group, in place of a 1-carbonyl group, bonded to the alpha nitrogen"

(ix) FEATURE:
   (A) NAME/KEY: Modified-site
   (B) LOCATION: 6
   (D) OTHER INFORMATION: /note= "(cont'd) of the subsequent amino acid"

(ix) FEATURE:
   (A) NAME/KEY: Modified-site
   (B) LOCATION: 7
   (D) OTHER INFORMATION: /note= "Xaa is Leucin-1-ol (Leu-OH)"

(xi) SEQUENCE DESCRIPTION: SEQ ID NO:18:

Asp Ser Phe Val Gly Xaa Xaa
1               5